(12) United States Patent
McClellan

(10) Patent No.: US 10,398,855 B2
(45) Date of Patent: Sep. 3, 2019

(54) AUGMENTED REALITY BASED INJECTION THERAPY

(71) Applicant: William T. McClellan, Morgantown, WV (US)

(72) Inventor: William T. McClellan, Morgantown, WV (US)

( * ) Notice: Subject to any disclaimer, the term of this patent is extended or adjusted under 35 U.S.C. 154(b) by 0 days.

(21) Appl. No.: 15/812,185

(22) Filed: Nov. 14, 2017

(65) Prior Publication Data

US 2019/0143052 A1 May 16, 2019

(51) Int. Cl.
| | |
|---|---|
| *A61M 5/42* | (2006.01) |
| *G06K 9/00* | (2006.01) |
| *G06F 19/00* | (2018.01) |
| *G06F 3/02* | (2006.01) |
| *G06F 3/16* | (2006.01) |

(52) U.S. Cl.
CPC ......... *A61M 5/427* (2013.01); *G06F 19/3468* (2013.01); *G06K 9/00255* (2013.01); *G06K 9/00671* (2013.01); *A61M 2205/3584* (2013.01); *A61M 2205/507* (2013.01); *G06F 3/0202* (2013.01); *G06F 3/167* (2013.01)

(58) Field of Classification Search
CPC . A61M 5/427; G06F 19/3468; G06K 9/00671
USPC ....................................................... 345/633
See application file for complete search history.

(56) References Cited

U.S. PATENT DOCUMENTS

| | | | |
|---|---|---|---|
| 8,605,008 B1 | 12/2013 | Prest et al. | |
| 9,646,511 B2 | 5/2017 | Jerauld | |
| 9,759,917 B2 | 9/2017 | Osterhout et al. | |
| 9,792,682 B2* | 10/2017 | Gluncic | G06T 7/0012 |
| 2005/0137584 A1 | 6/2005 | Lemchen | |
| 2005/0148935 A1 | 7/2005 | Dimitrova et al. | |
| 2006/0079745 A1* | 4/2006 | Viswanathan | A61B 5/062 600/407 |
| 2007/0038944 A1* | 2/2007 | Carignano | G06T 15/20 715/757 |
| 2008/0308732 A1* | 12/2008 | Warnke | G01N 25/72 250/330 |
| 2009/0173846 A1 | 7/2009 | Katz | |
| 2010/0079356 A1 | 4/2010 | Hoellwarth | |
| 2010/0118123 A1 | 5/2010 | Freedman et al. | |
| 2010/0290698 A1 | 11/2010 | Freedman et al. | |
| 2011/0160578 A1 | 6/2011 | Tripathi et al. | |
| 2012/0019511 A1 | 1/2012 | Chandrasekhar | |

(Continued)

*Primary Examiner* — Ryan R Yang

(74) *Attorney, Agent, or Firm* — Andrew D. Wright; Roberts Mlotkowski Safran Cole & Calderon, P.C.

(57) ABSTRACT

Approaches for augmented reality systems and methods for administering repeated injections are provided. An augmented reality (AR) system for administering injections includes: an AR headset comprising a display that is configured to display at least one marker superimposed on a real-world view of a subject, the at least one marker being displayed at a user-defined location on the subject. The display may be configured to continuously display the at least one marker at the location on the subject as the real-world view of the subject changes. The marker may be generated based on user input received from a user wearing the AR headset. The location on the subject may be defined by a location of a marker device relative to the subject when the user input is received. The AR headset may include a face mapping system.

25 Claims, 8 Drawing Sheets

(56) References Cited

U.S. PATENT DOCUMENTS

| | | | |
|---|---|---|---|
| 2013/0117161 A1* | 5/2013 | Waidmann | G06Q 30/06 |
| | | | 705/27.1 |
| 2013/0176336 A1* | 7/2013 | Hannula | A61B 5/0042 |
| | | | 345/633 |
| 2014/0088427 A1 | 3/2014 | Tashiro | |
| 2014/0121637 A1 | 5/2014 | Boyden et al. | |
| 2014/0333745 A1 | 11/2014 | Howard | |
| 2015/0243288 A1* | 8/2015 | Katsuranis | G06F 3/0484 |
| | | | 704/275 |
| 2015/0347849 A1* | 12/2015 | Vullioud | G06K 9/00671 |
| | | | 345/633 |
| 2015/0355463 A1* | 12/2015 | Sako | G02B 27/017 |
| | | | 345/633 |
| 2016/0136363 A1 | 5/2016 | McClellan | |
| 2016/0324580 A1* | 11/2016 | Esterberg | A61B 34/10 |
| 2017/0053447 A1 | 2/2017 | Chen et al. | |
| 2017/0109929 A1 | 4/2017 | Meier et al. | |
| 2017/0168568 A1 | 6/2017 | Petrov | |
| 2017/0235143 A1 | 8/2017 | Chi et al. | |
| 2018/0137678 A1* | 5/2018 | Kaehler | G02B 27/0093 |
| 2018/0218371 A1* | 8/2018 | Wang | G06Q 20/4014 |
| 2018/0296273 A1* | 10/2018 | Beck | A61B 34/10 |

\* cited by examiner

AUGMENTED REALITY BASED INJECTION THERAPY

BACKGROUND

The present invention generally relates to medical devices and procedures and, more particularly, to augmented reality systems and methods for administering repeated injections.

Subcutaneous and intramuscular administration of a botulinum toxin is used for treating various diseases and for cosmetic applications. Typically, a syringe or a needleless device is used to inject the botulinum toxin to the dermal or subdermal target tissue. For some diseases, such as neuralgia, multiple injections of the botulinum toxin can be required over a relatively small area of the skin. Multiple injections are carried out to achieve a desired distribution and therapeutic diffusion of the botulinum toxin into the target area, as opposed to making only one or a few injections.

Injection therapy is commonly carried out over a number of discrete procedures that may be separated by weeks or months. In one exemplary scenario, a patient indicates that the previous injection treatment was highly satisfactory and requests that the provider "do what you did last time," which essentially is a request to administer the injections of the current procedure in the exact same locations as the injections of the previous procedure. However, it is very difficult if not impossible for the provider to administer the injections in the exact same locations as they were administered in the previous office visit. This is because the provider is essentially going from memory as to where they administered the injections in the previous visit. As a result, it is nearly impossible to precisely repeat the same injections in the same locations from one injection treatment procedure to the next.

SUMMARY

In a first aspect of the invention, there is an augmented reality (AR) system for administering injections, comprising: an AR headset comprising a display that is configured to display at least one marker superimposed on a real-world view of a subject, the at least one marker being displayed at a user-defined location on the subject. In embodiments, the display is configured to continuously display the at least one marker at the location on the subject as the real-world view of the subject changes. In embodiments, the marker is generated based on user input received from a user wearing the AR headset. In embodiments, the location on the subject is defined by a location of a marker device relative to the subject when the user input is received. The user input may be: a voice command, a button press on the marker device, or based on a means to detect when the marker device comes into physical contact with the subject.

In embodiments, data defining the at least one marker is stored in computer memory. The data may define the location on the subject. The data may define at least one of: a size of the at least one marker, a shape of the at least one marker; and a color of the at least one marker. The system may be configured to receive user input to change at least one of: the location on the subject; a size of the at least one marker, a shape of the at least one marker; and a color of the at least one marker. In embodiments, the system is configured to: automatically identify the subject; in response to the automatically identifying the subject, access the data defining the at least one marker; and in response to the accessing the data, automatically display the at least one marker superimposed on another real-world view of a subject, the at least one marker being displayed at the user-defined location on the subject.

In an embodiment, the AR headset comprises a direct view device, the display is substantially transparent, the real-world view of the subject is seen through the substantially transparent display. In another embodiment, the AR headset comprises an indirect view device, and the real-world view of the subject is real-time camera imagery that is displayed via the display.

The AR headset may comprise a face mapping system. The face mapping system may comprise: an infrared emitter that projects a number of dots in a predefined pattern onto a surface of a person's face; and an infrared camera that photographs an image of the dots on the surface of the person's face. The location of the at least one marker on the subject may be defined relative to a facial map of the subject generated by the face mapping system.

The AR headset may comprise one of: goggles, glasses, a headband, and a helmet.

In another aspect of the invention, there is a method of using augmented reality (AR) for administering injections, comprising: receiving user input defining at least one marker at a location on a subject; and displaying, by a display of an AR headset, the at least one marker superimposed on a real-world view of the subject, the at least one marker being displayed at the user-defined location on the subject. The method may further comprise continuously displaying the at least one marker at the location on the subject as the real-world view of the subject changes.

BRIEF DESCRIPTION OF THE DRAWINGS

The present invention is described in the detailed description which follows, in reference to the noted plurality of drawings by way of non-limiting examples of exemplary embodiments of the present invention.

DETAILED DESCRIPTION

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description taken with the drawings making apparent to those skilled in the art how the several forms of the present invention may be embodied in practice.

The present invention generally relates to medical devices and procedures and, more particularly, to augmented reality systems and methods for administering repeated injections. Augmented reality (AR) is a live direct or indirect view of a physical, real-world environment whose elements are augmented by computer-generated imagery. Augmented reality may be implemented in wearable display systems that are embodied in a wearable headset that is arranged to display an image within a short distance from a human eye. Such wearable headsets are sometimes referred to as head mounted displays (HMDs). Optical components are arranged in a wearable headpiece so as to display the desired image within a few centimeters of the user's eyes.

Aspects of the invention leverage an AR system in an injection therapy methodology. Implementations of the invention utilize AR in a manner that advantageously permits a provider, such as a physician who is administering injection therapy to a patient, to precisely repeat the same injections in the same locations on the patient from one injection treatment procedure to the next.

Figure 1A:
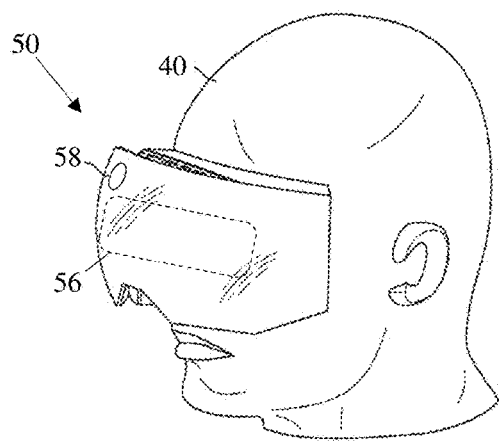
FIGS. 1A and 1B show exemplary shapes of an AR system in accordance with aspects of the invention.
Figure 1B:
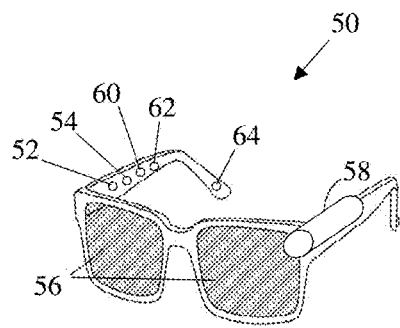

FIGS. 1A and 1B show examples of a wearable AR headset 50 in accordance with aspects of the invention. The headset 50 is arranged to display an image within a short distance from a human eye of a wearer 40. Different shapes of headset 50 may be used within the scope of the invention. For example, as shown in FIG. 1A the headset 50 may comprise a goggle-like shape, and as shown in FIG. 1B the headset 50 may comprise a glasses-like shape. Other shapes may also be used for the headset 50, including but not limited to a helmet and a headband.

Figure 2:
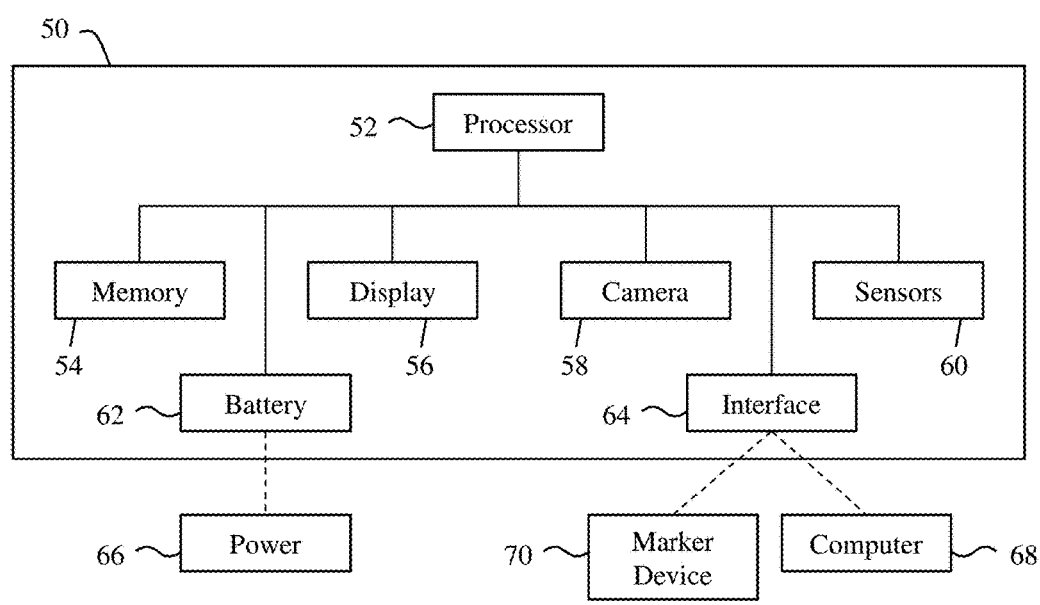
FIG. 2 shows a block diagram of an AR system in accordance with aspects of the invention.

FIG. 2 shows a block diagram of an AR system including the headset 50 in accordance with aspects of the invention. In embodiments, the AR system includes at least one computer processor 52, at least one computer memory 54, at least one visual display 56, at least one camera 58, and at least one sensor 60. These components, and the circuitry that operatively connects them, may be embedded in and/or attached to a structural member of the headset 50 (e.g., a glasses/goggles frame, headband, etc.), as diagrammatically shown in FIG. 1B. Similarly, although not shown, these components and the circuitry that operatively connects them may be embedded in and/or attached to a structural member of the headset 50 of FIG. 1A and any other headset used in implementations of the invention.

Processor 52 may comprise any number and suitable type of processing unit including without limitation a CPU, a GPU, and an FPGA. Memory 54 may comprise any suitable type of memory, such as RAM, cache, and flash memory, for example. Memory 54 may store, by way of example and not limitation, an operating system, one or more application programs, other program modules, and program data, which may be executed by the processor 52 to carry out one or more of the functions described herein.

Display 56 comprises one or more display elements that are configured to display a visual image within a short distance from a human eye of a wearer 40. Display 56 may comprise, but is not limited to, a waveguide display, a projection display, and an LCD display.

In embodiments, the camera 58 comprises at least one forward facing camera that is configured to capture video imagery of the real-world environment that is in front of the wearer 40. In a preferred embodiment, the camera 58 comprises two forward facing cameras, and in a more preferred embodiment the camera 58 comprises two forward facing stereo cameras configured to capture an approximate view (e.g., field of view) from the wearer's left and right eyes respectfully. The two stereo cameras may be located towards either side of the wearer's head on the headpiece, and thus capture images of the scene forward of the device form slightly different perspectives. In combination, the stereo cameras capture a stereoscopic moving image of the real-world environment within the field of view of the wearer.

In embodiments, the at least one sensor 60 is configured to determine a spatial position of the headset 50 in six degrees of freedom comprising: Cartesian coordinates (x,y, z) of the headset 50 with respect to a suitable origin; and roll, pitch, and yaw (R, P, Y) of the headset 50 with respect to suitable reference axes relative to the origin. The at least one sensor 60 may comprise at least one of an accelerometer, a gyro, a compass, a GPS sensor, and a proximity sensor. Any suitable sensor technology may be used, including but not limited to MEMS (microelectromechanical systems) sensors.

The electrical components of the headset 50 may be powered by a battery 62 that is carried by (or part of) the headset 50. Alternatively, the headset 50 may be physically wired to an electrical power source 66 that provides power to the electrical components of the headset 50.

The headset 50 may include an interface 64, which may be a wired and/or wireless communication interface by which the headset 50 communicates with another computer device 68 and/or a marker device 70. For example, the interface 64 may comprise at least one antenna that is configured for wireless communication between the headset 50 and another computer device 68 and/or a marker device 70 via at least one of WiFi, Bluetooth, NFC, etc. Additionally, or alternatively, the interface 64 may comprise a wired link between the headset 50 and another computer device 68 and/or a marker device 70.

The headset 50 may be configured as either a direct view AR device or an indirect view AR device. In the direct view configuration, the user 40 wearing the headset 50 sees through a substantially transparent display 56, and AR objects are rendered on the display 56 in locations that coincide with the real-world object that is being directly viewed through the display. When the headset 50 comprises a direct view device, the AR rendering may be performed using hardware and techniques such as that described U.S. Patent Application Publication No. 2017/0053447, dated Feb. 23, 2017, the disclosure of which is incorporated by reference herein its entirety. For example, in the direct view implementation, the display 56 may comprise an at least one optical component that is a substantially transparent waveguide, whereby the wearer can see through it to view a real-world environment in which they are located simultaneously with a projected AR object, thereby providing an augmented reality experience. Other direct view rendering displays may also be used.

In the indirect view configuration, the user wearing the headset 50 does not see the real-world environment through the display 56. Instead, in the indirect view configuration, the display 56 shows real-time imagery of the real-world environment captured by the at least one camera, and AR objects are simultaneously rendered on the display 56 in locations that coincide with objects contained in the imagery of the real-world environment captured by the at least one camera. In this manner, the wearer sees a view of the real-world environment indirectly, i.e., via camera, simultaneously with an AR object, thereby providing an augmented reality experience.

The details of the electronics and optics of the display system, including the AR object rendering, are not the subject of this invention, and any conventional or laterdeveloped display and rendering system and/or technique may be used in implementations of the invention. Descriptions of various types of electronics and optics of an AR system are provided in U.S. Patent Application Publication No. 2017/0053447, dated Feb. 23, 2017, U.S. Patent Application Publication No. 2017/0109929, dated Apr. 20, 2017, U.S. Patent Application Publication No. 2017/0235143, dated Aug. 17, 2017, and U.S. Pat. No. 9,646,511 issued May 9, 2017, each of which is incorporated by reference herein in its entirety.

In embodiments, the processor 52 and the memory 54 are embedded in and/or attached to the headset 50, e.g., as depicted in FIG. 1B. Alternatively, either or both of these elements may be contained in a separate housing connected to the components of the headset 50 by wired and/or wireless means. For example, the separate housing may be designed to be worn on a belt or to fit in the wearer's pocket, or one or more of these components may be housed in a separate computer 68 (e.g., smartphone, tablet, laptop or desktop computer etc.) which communicates wirelessly with the display 56 and camera 58 in the headset 50 (e.g., via interface 64), whereby the headset 50 and separate device constitute the AR system.

FIGS. 3A, 3B, 4A, 4B, 5A, 5B, 6A, 6B, 7A, and 7B illustrate functionality of the AR system in accordance with aspects of the invention. These figures are shown with the goggle-like headset 50 of FIG. 1A, but it is understood that the functionality described in these figures can be implemented in the glasses-like headset 50 of FIG. 1B and other shapes of headset 50.

Figure 3A:
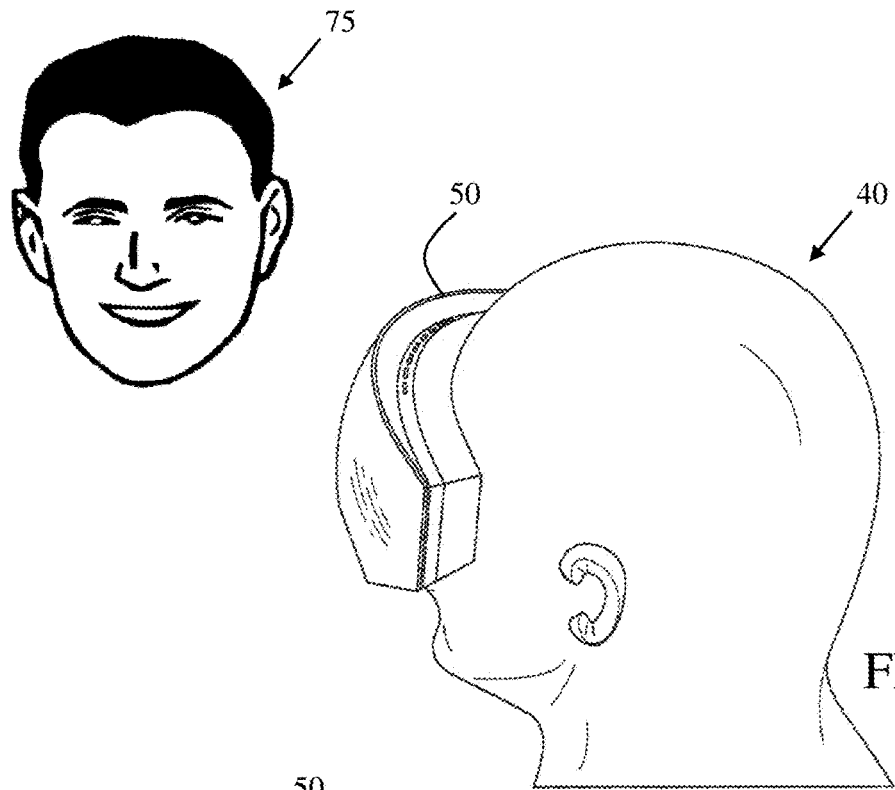
FIGS. 3A, 3B, 4A, 4B, 5A, 5B, 6A, 6B, 7A, and 7B illustrate functionality of the AR system in accordance with aspects of the invention.
Figure 3B:
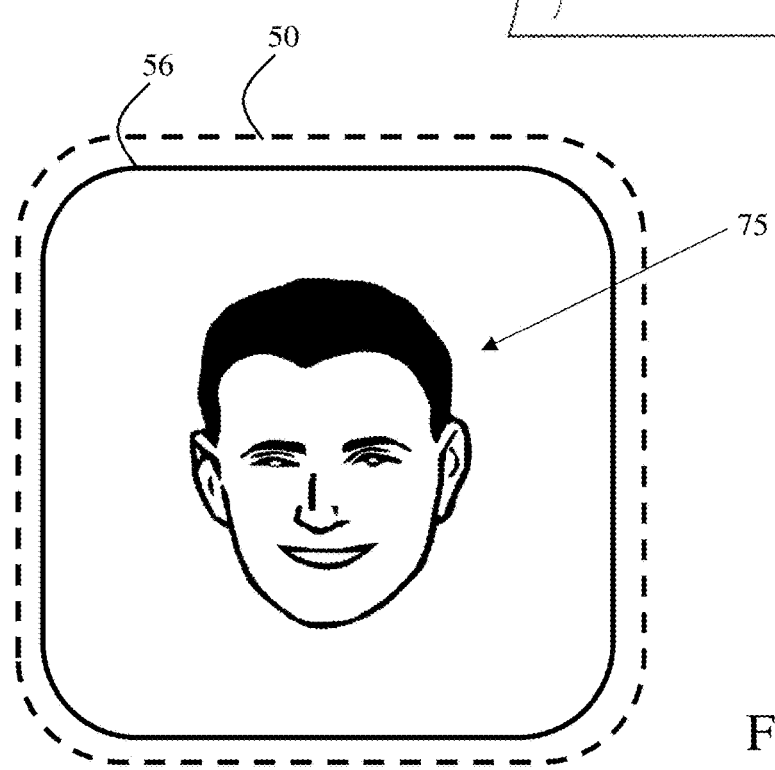

In each of the pairs of figures (FIGS. 3A-B, FIGS. 4A-B, FIGS. 5A-B, FIGS. 6A-B, FIGS. 7A-B), the "A" figure depicts a real-world environment, and the "B" figure depicts the corresponding view of what the user 40 sees via the display 56 of the headset 50. For example, FIG. 3A depicts the real-world environment of a user 40 wearing the headset 50 and looking in the direction of a patient 75 (also referred to as a subject). FIG. 3B shows the display 56 of the headset 50 corresponding to the real-world environment depicted in FIG. 3A. In a direct view implementation, FIG. 3B depicts the user 40 seeing the patient 75 through the substantially transparent display 56. In an indirect view implementation, FIG. 3B depicts the display 56 showing a real-time image of the patient 75 the, the image of the patient 75 being captured in real-time by the one or more cameras 58 of the headset 50. In both direct view and indirect view implementations, if either one of the user 40 and/or the patient 75 move relative to one another, the view through (or shown on) the display 56 will change in real-time, as is understood in AR systems.

Figure 4A:
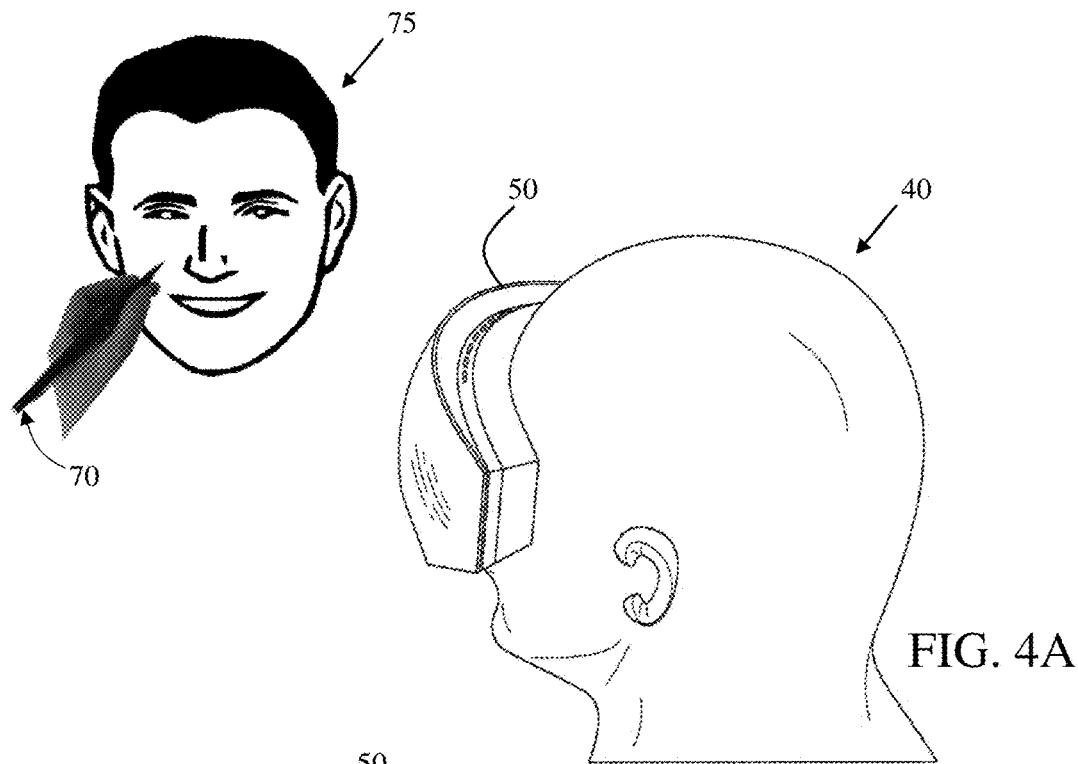
Figure 4B:
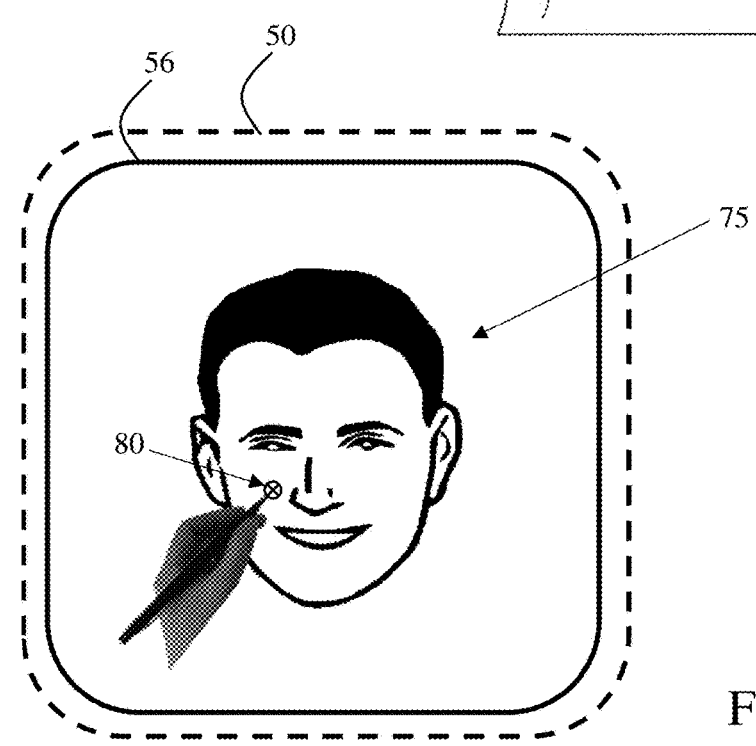

FIGS. 4A and 4B illustrate a continuation of the example from FIGS. 3A and 3B. As shown in FIG. 4A, the user 40 manipulates a marker device 70 to a location near/on the face of the patient 75. As shown in FIG. 4B, the user 40 sees (via the display 56) the movement and location of the marker device 70 relative to the patient 75 in real-time, e.g., the user 40 continues to see the real-world environment in real-time via the display 56.

Still referring to FIG. 4B, according to aspects of the invention, the user 40 may provide an input to the system to generate a marker 80 relative to the patient 75 as viewed via the display 56. The marker 80 is a computer generated visual object that is overlaid onto the real-world environment that is viewed via the display 56. In embodiments, the marker 80 is displayed on the patient's face 75 at a location that coincides with a distal tip of the marker device 70. In this manner, the user 40 may utilize the marker device 70 to selectively indicate locations (represented by markers 80) for injection therapy on the patient 75. In this manner, the location of the marker 80 on the patient 75 is defined by a location of a marker device 70 relative to the patient 75 when the user input is received.

The user input to generate the marker 80 may take different forms. In a first example, the marker device 70 may comprise a button that the user 40 selects to provide the input. In this example, when the user 40 presses the button, the marker device 70 sends a signal to the processor 52 (via the interface 64), an application program/module being executed by the processor 52 generates the marker 80 based on the input, and the processor 52 causes the display 56 to visually show the marker 80 superimposed on the real-world environment that is viewed via the display 56.

In another example of the user input to generate the marker 80, the distal end of the marker device 70 comprises a means to detect when the marker device 70 comes into physical contact with the patient 75. The means may comprise, for example, a depressible tip at the distal end of the marker device 70, the depressible tip being connected to an electrical circuit that generates the input based on the tip being depressed when it contacts the patient. The means may comprise, in another example, an electrical sensor at the distal end of the marker device 70, the sensor being configured to electrically detect physical contact with human skin, the sensor being connected to an electrical circuit that generates the input based on the sensor detecting contact with the patient. In these examples, in response to the means detecting the marker device 70 comes into physical contact with the patient 75, the marker device 70 sends a signal to the processor 52 (via the interface 64), an application program/module being executed by the processor 52 generates the marker 80 based on the signal, and the processor 52 causes the display 56 to visually show the marker 80 superimposed on the real-world environment that is viewed via the display 56.

In another example of user input to generate the marker 80, the system may be configured detect when the user 40 speaks a predefined word or phrase, and to generate the marker 80 based on such detecting. For example, the headset 50 or a connected computer device 68 may include a microphone (not shown) that is configured to receive audio input, such as words spoken by the user 40. An application program/module being executed by the processor 52 may be programmed to analyze the audio data received at the microphone to detect predefined keywords or phrases in the audio data. When one of the predefined keywords or phrases is spoken and detected in this manner, the application program/module being executed by the processor 52 generates the marker 80 based on the detecting, and the processor 52 causes the display 56 to visually show the marker 80 superimposed on the real-world environment that is viewed via the display 56.

In accordance with aspects of the invention, an application program/module executed by the processor 52 is configured to determine a location of the distal end of the marker device 70 relative to the face of the patient 75 for the purpose of determining a location of the marker 80 on the patient 75. This location determination may be performed using data from the sensors 60 in the headset 50 and, optionally, using data from sensors in the marker device 70 that are configured to communicate with the sensors 60 in the headset 50. For example, one or more proximity sensors may be used to determine a distance from the headset 50 to the patient 75, and also a distance from the headset to the marker device 70. Image processing of the real-time imagery obtained by the at least one camera 58 may be used to identify a position of the marker device 70 relative to the face of the patient 75. Image processing of imagery obtained by the at least one camera 58 may be used to generate a facial mapping of the patient 75. Combinations of this data may be used to determine a location on the face of the patient 75 that corresponds to the marker 80 that is generated using the marker device 70 and user input. In embodiments, the system stores the determined location of a marker 80, e.g., in memory 54 or memory at the computer 68.

Figure 5A:
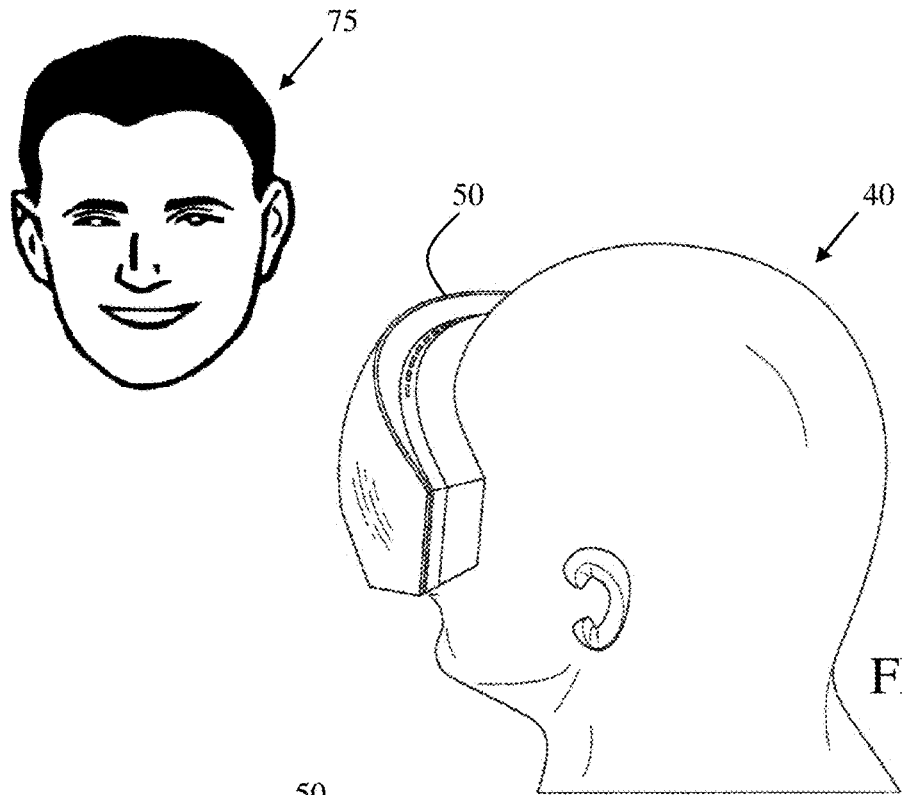
Figure 5B:
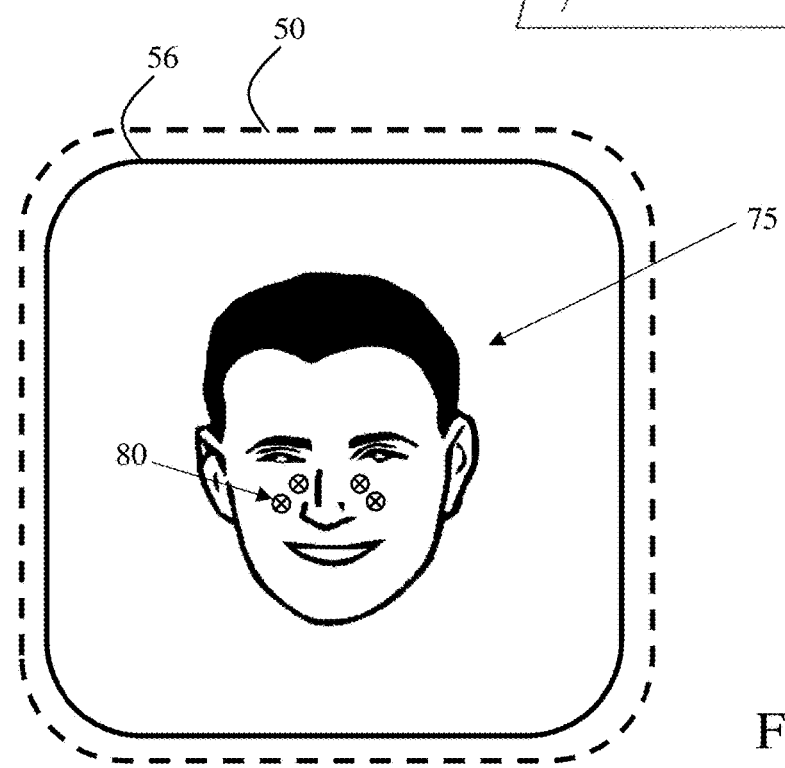

FIGS. 5A and 5B illustrate a continuation of the example from FIGS. 4A and 4B. As shown in FIG. 5B, the user 40 has generated four markers 80 on the face of the patient 75 (e.g., using the marker device 70 and user input as described above). As shown in FIG. 5A, the marker device 70 is no longer near the face of the patient 75 (e.g., the user 40 has moved it away). As shown in FIG. 5B, the user 40 continues to see the real-world environment in real-time via the display 56, with the added images of the four markers 80 superimposed on the face of the patient 75.

As described herein, the system determines and saves a location on the patient's face for each of the markers 80. In this manner, the system can be configured to constantly display the markers 80 on the same respective locations of the face of the patient 75 even when one of the user 40 and the patient 75 change positions relative to one another.

Figure 6A:
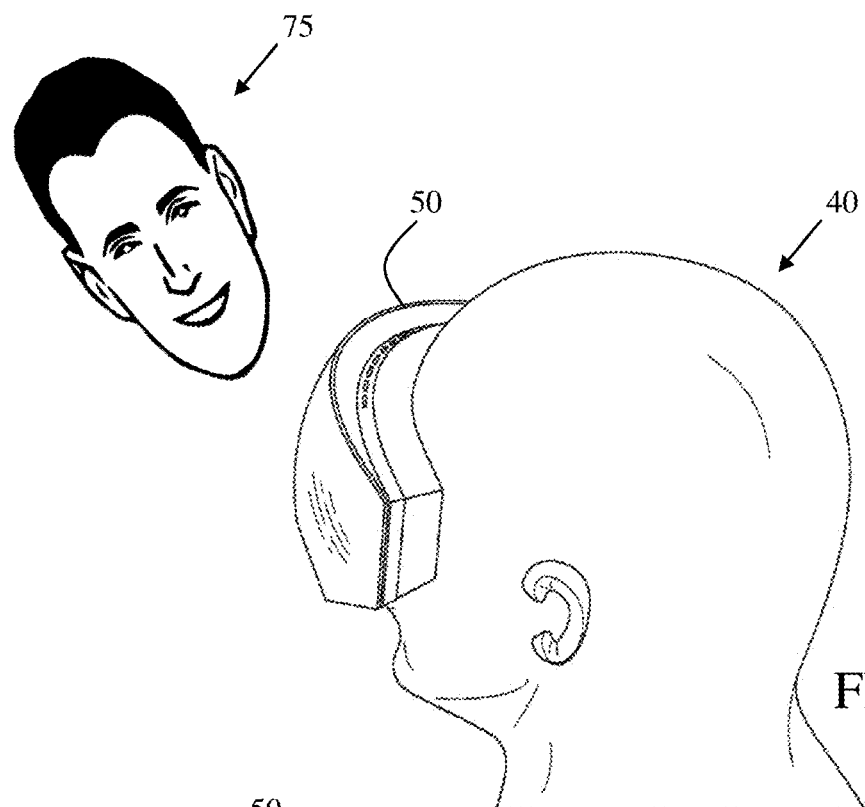
Figure 6B:
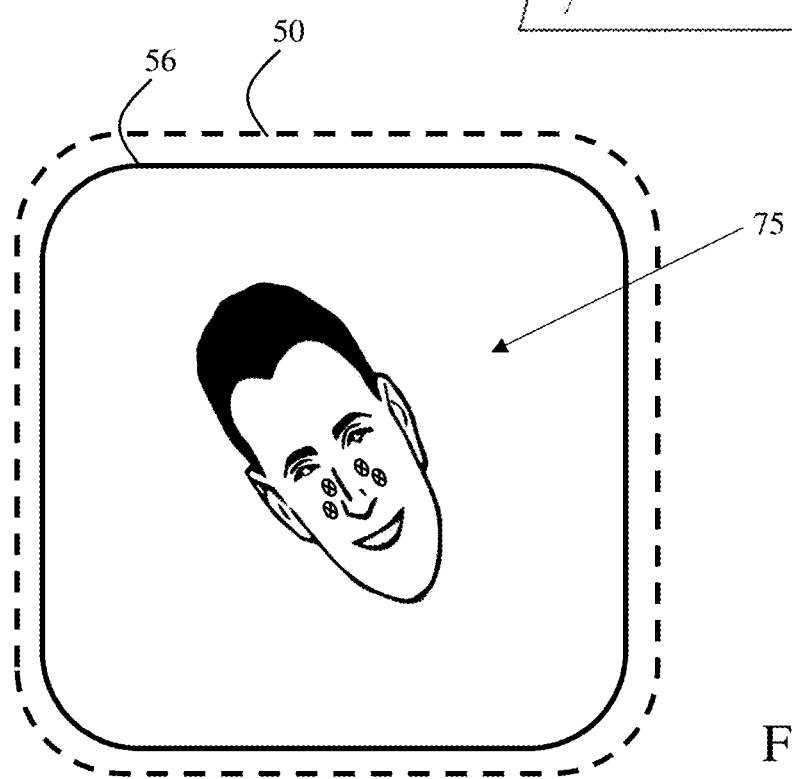

For example, as shown in FIGS. 6A and 6B, which are a continuation of the example from FIGS. 5A and 5B, the patient 75 and the user 40 have moved relative to one another. Stated differently, the user 40 is viewing the patient from a first direction in FIG. 5A and from a second direction, different from the first direction, in FIG. 6A. As shown in FIG. 6B, the user 40 continues to see the real-world environment in real-time via the display 56, e.g., the user 40 sees the patient from the second direction corresponding to the real-world environment depicted in FIG. 6A. According to aspects of the invention, the system displays the markers 80 moving in real-time with the face of the patient (e.g., moving from that shown in FIG. 5B to that shown in FIG. 6B), such that the display 56 shows the markers 80 at the same locations of the patient's face when the patient's face is moving due to relative movement between the patient 75 and the user 40.

In embodiments, the application program/module executed by the processor 52 is configured to perform continuous image processing of the real-time data obtained by the at least one camera 58, and to continuously update the displayed positions of the markers 80 based on the image processing and the previously determined locations of the markers 80 relative to the face of the patient 75. In a preferred embodiment, the system is configured to continuously update the displayed positions of the markers 80 based on the image processing, the previously determined locations of the markers 80 relative to the face of the patient 75, and a determined facial mapping of the patient 75. In this manner, the user 40 may move relative the patient 75 (e.g., as is common during treatment) and continue to see the markers 80 on the same locations of the patient's face via the display 56 during such movement. In this manner, the display is configured to continuously display the at least one marker 80 at the location on the patient 75 as the real-world view of the subject changes.

Figure 7A:
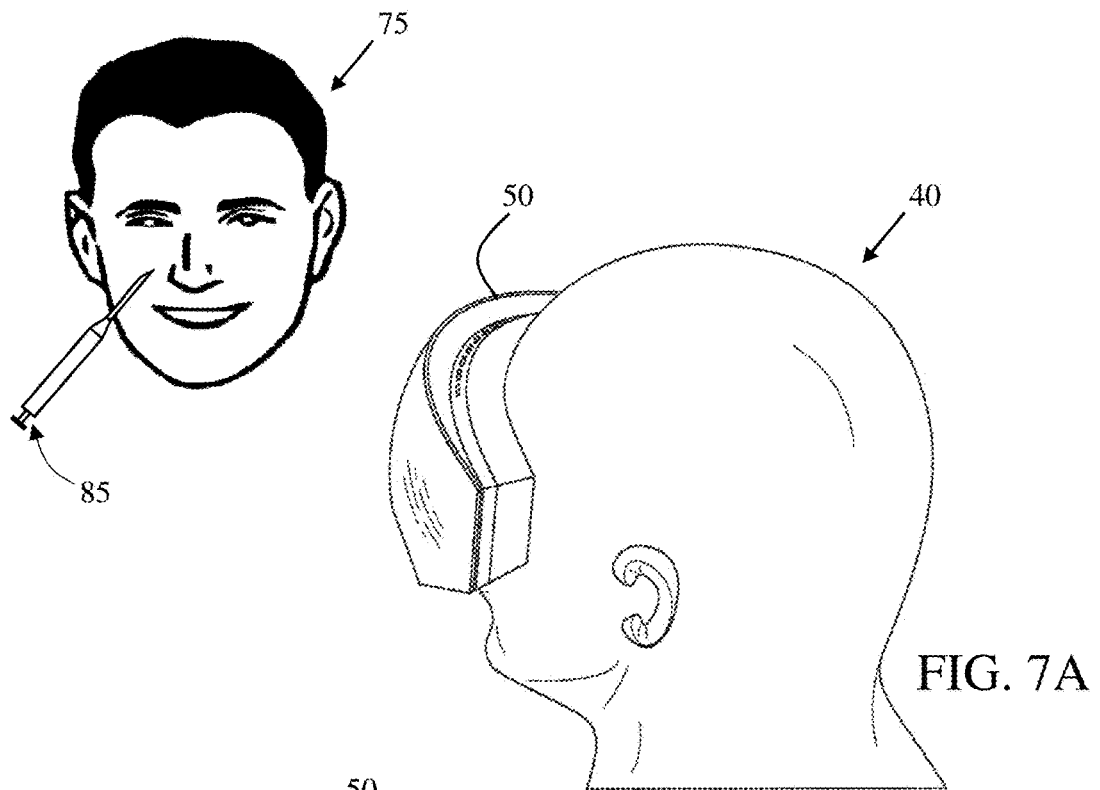
Figure 7B:
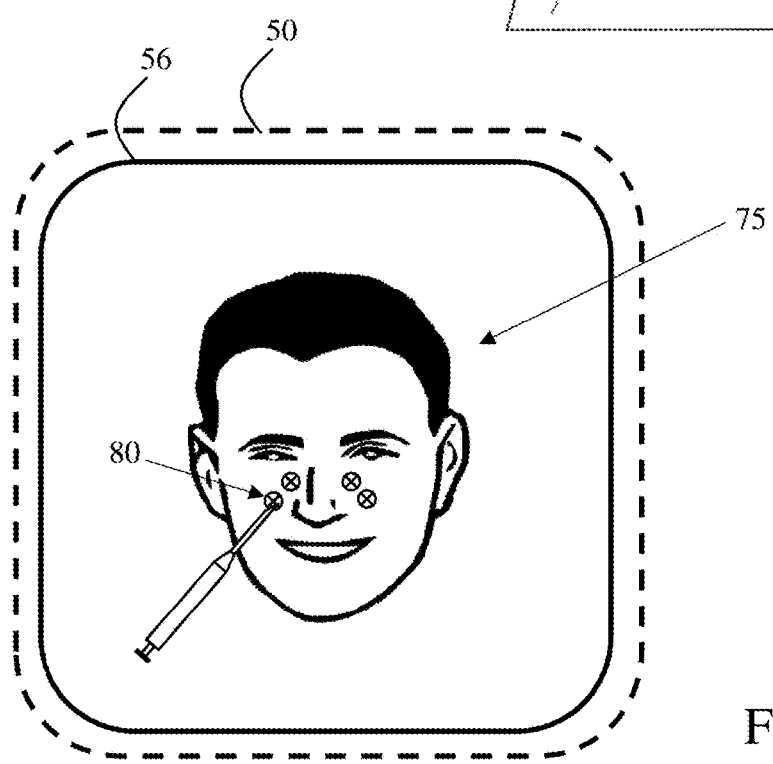

FIGS. 7A and 7B illustrate a continuation of the example from FIGS. 6A and 6B. As depicted in FIG. 7A, the user 40 wearing the headset 50 may manipulate an injection device 85 (e.g., a syringe) to administer injection therapy to the patient 75. As shown in FIG. 7B, the display 56 of the headset 50 shows the real-world environment and the markers 80 superimposed on the determined locations of the patient's face as described herein. The user 40 may utilize the markers 80 as target locations for injections via the injection device 85. For example, as the user 40 moves the injection device 85 relative the patient 75, the user 40 can see via the display 56 when the injection device 85 (e.g., a distal end of a needle of a syringe) is at one of the markers 80.

According to aspects of the invention, the system stores data defining the locations of the markers 80 relative to the face of the patient 75. The data may define the location of the marker 80 on the patient 75. The data may also define at least one of: a size of the marker, a shape of the marker; and a color of the marker. In an exemplary method of use, the markers 80 are generated during a first visit (e.g., at time t1), and stored in a patient profile. The patient returns at a later date for a second visit (e.g., at time t2 which may be days, weeks, or months later than t1). During the second visit, the system utilizes the stored data in the patient profile to display the markers 80 via the display 56 in the same locations on the patient's face as at the first visit. In this manner, the user 40 may utilize the system to perform repeated injections at same locations on the patient's face, even when the injections are spaced apart by long periods of time between visits.

The markers 80 may have any desired shape, including but not limited to: dots, geometric shapes (e.g., circle, triangle, square, n-gon), lines, alphabet characters, and numeral characters. Different shaped markers may be used on a same patient to indicate different aspects of treatment. The system may be configured to permit the user to provide user input (e.g., voice command, hand gesture, or computer 68) to select a shape from plural predefined shapes for a marker 80.

The markers 80 may have any desired size. Different sized markers may be used on a same patient to indicate different aspects of treatment. The system may be configured to permit the user to provide user input (e.g., voice command or computer 68) to select a size from plural predefined sizes for a marker 80.

The markers 80 may have any desired color. Different color markers may be used on a same patient to indicate different aspects of treatment. The system may be configured to permit the user to provide user input (e.g., voice command or computer 68) to select a color from plural predefined color for a marker 80.

In embodiments, the system is configured to permit the user to provide input to change one or more of the markers 80. For example, the system may be configured to show the markers 80 on an interface of the computer 68, and permit the user to provide input (e.g., via touch screen, mouse, keyboard, etc.) to perform any one or more of the following changes to a selected marker 80: move the marker to another location in the patient face; delete the marker from the patient profile; change the shape of the marker; change the size of the marker, or change the color of the marker. In another example, the system may be configured to permit the user to provide input to change/delete existing markers while the user is viewing the markers via the display 56. The user input in this example may be, for example, predefined voice commands, predefined hand gestures, etc. that are recognized by the system and that are programmed to cause predefined changes to one of the markers 80. Any such changes to the existing markers are stored as data in the patient profile.

Figure 8:
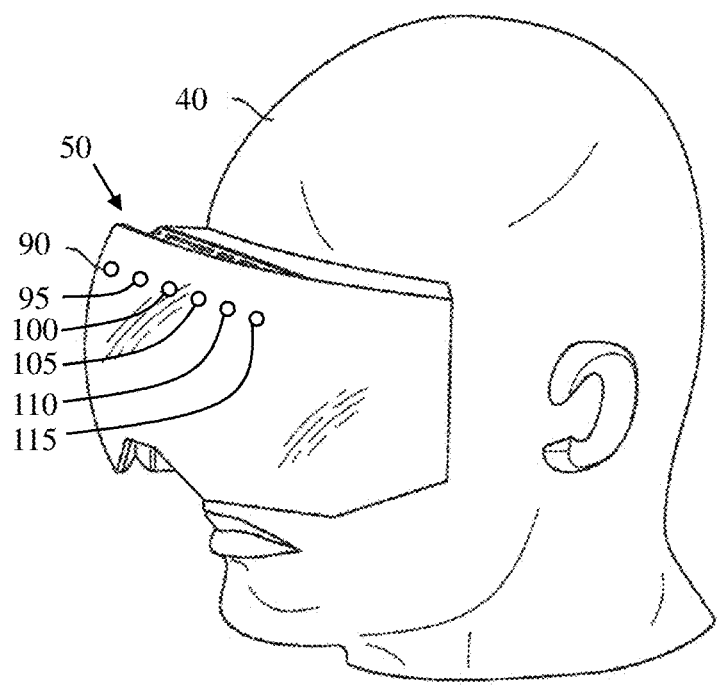
FIGS. 8 and 9 show aspects of a recognition system usable with an AR system in accordance with aspects of the invention.

In embodiments, the system may be configured to determine a facial map of the patient 75. The system may include hardware and be programmed with software to perform the face mapping. For example, the system may perform face mapping in a manner similar to the Kinect system by Microsoft Corporation of Redmond, Wash., or the IphoneX system of Apple Inc. of Cupertino, Calif. For example, as shown in FIG. 8, the headset 50 may include a flood illuminator 90, infrared camera 95, front camera 100, dot projector 105, proximity sensor 110, and ambient light sensor 115. In embodiments, the dot projector 105 comprises an infrared emitter that projects a number of dots (e.g., over 30,000 dots) in a predefined pattern onto a person's face. The infrared camera 95 photographs the image of the dots on the surface of the person's face. The processor 52 runs an application program/module that is configured to determine a surface mapping of the person's face based on comparing the predefined pattern of the projected dots to the image of the dots captured by the infrared camera 95. The front camera 100 and the infrared camera 95 may corresponds to the at least one camera 58 described with respect to FIG. 2.

Figure 9:
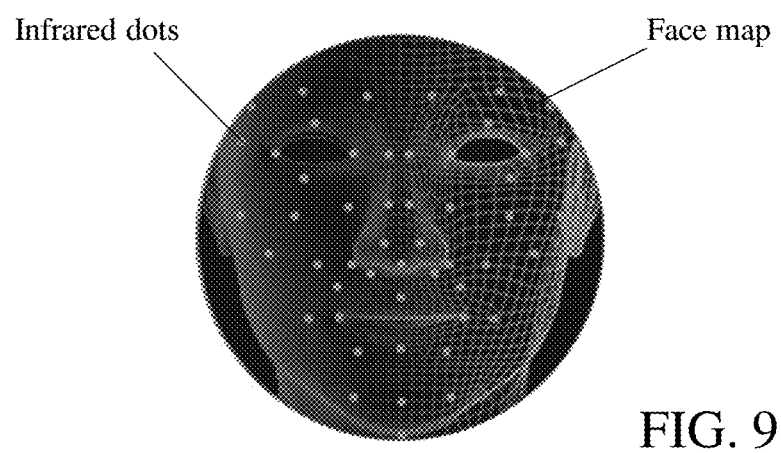

FIG. 9 shows an example of infrared dots projected onto a person's face and a representation of a face map generated using the face mapping technique described with respect to FIG. 8. In this manner, the headset 50 may be used to generate a 3-D face mapping of the patient 75, and data defining the face map may be stored in the patient profile. The data defining the locations of the markers 80 may be defined in terms of the stored face map.

In embodiments, the system may be configured to automatically determine the identity of a patient and access the patient profile, including the face map and defined locations of markers 80, based on the automatic identification. For example, processor 52 may run an application program/module that is configured to identify a patient using facial recognition techniques using the face map, other facial image processing, retinal identification, etc. Based on identifying the patient, the system may be configured to access the patient profile for the identified patient and automatically display (via the display 56) this patient's markers 80 superimposed on the patient's face. Additionally, or alternatively, the system may be configured to permit the user to provide user input (e.g., voice command or computer 68) to select input the identity of the patient and, based on this input, to access the patient profile for the identified patient and automatically display the markers 80 (via the display 56) that correspond to this patient.

Figure 10:
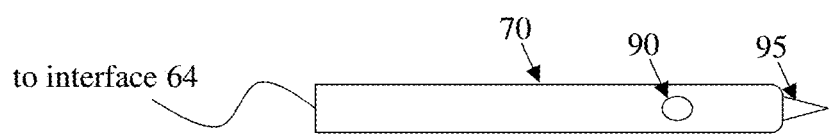
FIG. 10 shows an exemplary marker device in accordance with aspects of the invention.

FIG. 10 shows an exemplary marker device 70 in accordance with aspects of the invention. In embodiments, the marker device 70 comprises a stylus. As described herein, the marker device 70 may include a button 90 that is operatively connected to circuitry within the device that generates a user input signal when the button is pressed. As described herein, the marker device 70 may include a means 95 to detect when the marker device 70 comes into physical contact with the patient 75. The means 95 may comprise, for example, a depressible tip at the distal end of the marker device 70, the depressible tip being connected to an electrical circuit that generates the input based on the tip being depressed when it contacts the patient. The means 95 may comprise, in another example, an electrical sensor at the distal end of the marker device 70, the sensor being configured to electrically detect physical contact with human skin, the sensor being connected to an electrical circuit that generates the input based on the sensor detecting contact with the patient. The marker device 70 may communicate with the interface 64 via wired or wireless connection.

Figure 11:
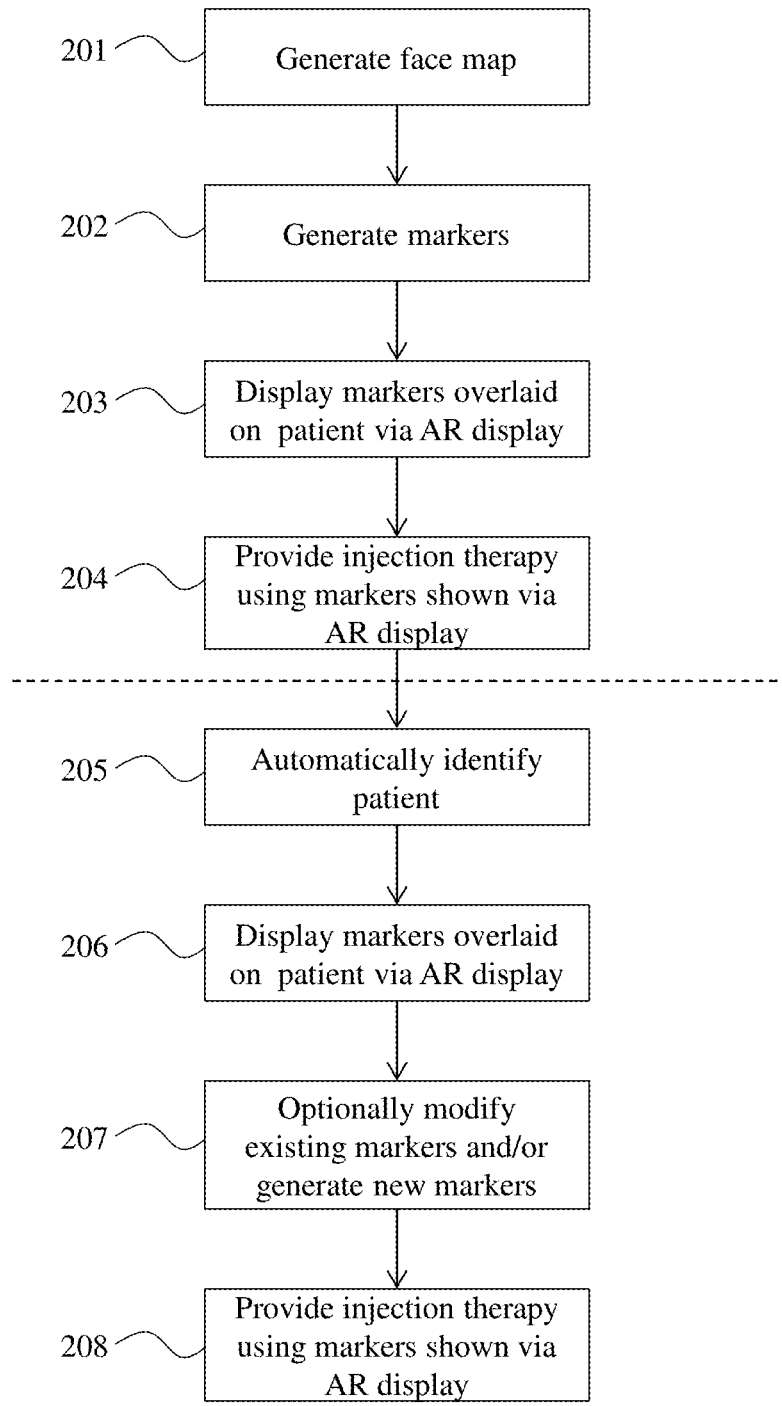
FIG. 11 shows a flowchart of a method in accordance with aspects of the invention.

FIG. 11 shows a flowchart of a method in accordance with aspects of the invention. The steps of FIG. 11 may be implemented using an AR system as described herein, for example, and are described using reference numbers of elements depicted in FIGS. 1-10. The flowchart illustrates the architecture, functionality, and operation of possible implementations of systems, methods, and computer program products according to various embodiments of the present invention.

At step 201, the AR system generates a face map of a patient. The face map may be generated in the manner described with respect to FIGS. 8 and 9, or using other face mapping techniques. Data defining the face map may be stored in a patient profile for the patient being mapped.

At step 202, the AR system generates one or more markers 80, e.g., in the manner described herein with respect to FIGS. 4A and 4B. At step 203, the display 56 of the AR system displays the markers 80 overlaid on the patient, e.g., as described with respect to FIGS. 5A, 5B, 6A, 6B. At step 204, the user 40 wearing the headset 50 of the AR system provides injection therapy to the patient while viewing the patient 75 and the markers 80 via the display 56, e.g., as described with respect to FIGS. 7A and 7B.

In an exemplary method, steps 201-204 may be performed at a first visit, and steps 205-208 may be performed at a second visit. At step 205, the patient returns for the second visit and the AR system automatically identifies the patient. In embodiments, the automatic identification is performed using the face map from step 201, e.g., in the manner described herein, or by using other camera and computer-based automatic recognition techniques.

At step 206, the display 56 of the AR system displays the markers 80 overlaid on the patient, e.g., as described with respect to FIGS. 5A, 5B, 6A, 6B. In embodiments, after recognizing the patient at step 205, the AR system accesses the patient profile, obtains data defining the markers 80 for this patient, and displays the markers 80 at the defined locations on the patient's face as seen via the display 56.

At step 207, the user may optionally modify one or more of the existing markers 80 and/or may add at least one new marker 80. For example, as described herein, the user may provide input to change the size/shape/color/location of an existing marker 80 that is displayed by the display 56. Additionally, or alternatively, the user may provide user input to delete an existing marker 80 that is displayed by the display 56. Additionally, or alternatively, the user may provide user input to generate a new marker 80, e.g., in the manner similar to step 202.

At step 208, the user 40 wearing the headset 50 of the AR system provides injection therapy to the patient while viewing the patient 75 and the markers 80 via the display 56, e.g., as described with respect to FIGS. 7A and 7B.

Implementations of the invention may be used to provide accuracy and repeatability in administering injections to a subject. Aspects may be used to provide targeted treatment of: brow lines, glabella furrows, crows feet, nasojugal folds, nasolabial folds, marionette lines, chin line, and platysmal bands. Implementations of the invention are not limited to use with the face of a subject, and instead may be used on any part of a subject. Aspects described herein permit the provider to reproduce injections over multiple visits and/or alter injection habits in order to maximize the subject results.

Implementations of the invention may be used with different types of injection therapy. For example, aspects may be used to provide targeted injection therapy with: neurotoxins, subcutaneous dermal enhancers, insulin, antibiotics, hormones, chemotherapeutic agents, anti-inflammatory agents, other biological agents, Botox, subdermal filler such as Restylane, Juvederm, etc.

An aspect of the invention includes an AR system comprising the headset 50 programmed with logic (e.g., an application program/module) that causes the headset to perform one or more of the functions described herein. Another aspect of the invention includes a computer program product, provided as a physical storage medium or as a download, that is configured to be executed by an AR headset (or by a computer device connected to an AR headset) to cause the AR headset to perform one or more of the functions described herein. Another aspect of the invention includes an AR system comprising both the marker device 70 and the headset 50 programmed with logic (e.g., an application program/module) that causes the headset to perform one or more of the functions described herein. Another aspect of the invention includes a kit comprising the marker device 70 and a computer program product, provided as a physical storage medium or as a download, that is configured to be executed by an AR headset (or by a computer device connected to an AR headset) to cause the AR headset to perform one or more of the functions described herein. Another aspect of the invention includes a method of providing targeted injection therapy as described herein. The computer program product may comprise a computer readable storage medium having program instructions embodied therewith, the program instructions executable by a computing device to cause the computing device to perform one or more functions described herein.

It is noted that the foregoing examples have been provided merely for the purpose of explanation and are in no way to be construed as limiting of the present invention. While the present invention has been described with reference to an exemplary embodiment, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed is:

1. A augmented reality (AR) system for administering injections to a person, comprising:
   an AR headset comprising a display that is configured to display at least one marker superimposed on a real-world view of the person, the at least one marker being displayed at a user-defined location on the person, and the at least one marker defining a location of an injection into the person.

2. The system of claim 1, wherein the display is configured to continuously display the at least one marker at the location on the person as the real-world view of the person changes through the AR headset.

3. The system of claim 1, wherein the marker is generated based on user input received from a user wearing the AR headset.

4. The system of claim 3, wherein the location on the person is defined by a location of a marker device relative to the person when the user input is received.

5. The system of claim 4, wherein the user input is a voice command from the user wearing the AR headset.

6. The system of claim 4, wherein the user input is a button press on the marker device.

7. The system of claim 4, wherein the user input is based on a means to detect when the marker device comes into physical contact with the person.

8. The system of claim 1, wherein data defining the at least one marker is stored in computer memory.

9. The system of claim 8, wherein the data defines the location on the person.

10. The system of claim 8, wherein the data defines at least one of: a size of the at least one marker, a shape of the at least one marker; and a color of the at least one marker.

11. The system of claim 8, wherein the system is configured to receive user input to change at least one of: the location on the person; a size of the at least one marker, a shape of the at least one marker; and a color of the at least one marker.

12. The system of claim 8, wherein the system is configured to:
    automatically identify the person;
    in response to the automatically identifying the person, access the data defining the at least one marker; and
    in response to the accessing the data, automatically display the at least one marker superimposed on another real-world view of the person, the at least one marker being displayed at the user-defined location on the person, such that at a second visit the at least one marker is displayed at a same location on the person's face as it was during a first visit to facilitate providing an injection at the same location on the person's face during both the first visit and the second visit.

13. The system of claim 1, wherein:
    the AR headset comprises a direct view device;
    the display is substantially transparent; and
    the real-world view of the person is seen through the substantially transparent display.

14. The system of claim 1, wherein:
    the AR headset comprises an indirect view device; and
    the real-world view of the person is real-time camera imagery that is displayed via the display.

15. The system of claim 1, wherein the AR headset comprises a face mapping system.

16. The system of claim 15, wherein the face mapping system comprises:
    an infrared emitter that projects a number of dots in a predefined pattern onto a surface of the person's face; and
    an infrared camera that photographs an image of the dots on the surface of the person's face.

17. The system of claim 1, wherein the AR headset comprises one of: goggles, glasses, a headband, and a helmet.

18. The system of claim 1, wherein:
    the AR headset comprises a face mapping system that is configured to generate a facial map of the person;
    the at least one marker is generated based on user input received from a user wearing the AR headset;
    the location of the at least one marker on the person is: (i) defined by a location of a marker device relative to the person when the user input is received, and (ii) defined relative to the facial map of the person generated by the face mapping system.

19. The system of claim 18, wherein, after both the facial map and the at least one marker are generated, the system is configured to:
    automatically identify the person using the facial map;
    in response to the automatically identifying the person, access stored data defining the at least one marker relative to the facial map of the person; and in response to the accessing the data, automatically display the at least one marker superimposed on another real-world view of the person, the at least one marker being displayed at the user-defined location on the person.

20. The system of claim 18, wherein:
the AR headset displays the at least one marker moving in real-time with the face of the person such that the AR headset displays the at least one marker at the same location of the person's face when the person's face is moving due to relative movement between the person and the AR headset.

21. The system of claim 18, wherein:
the system is configured to continuously update a displayed position of the at least one marker based on: image processing of real-time data obtained by at least one camera; a previously determined location of the at least one marker relative to the face of the person; and the facial map of the person.

22. The system of claim 1, wherein:
the system is configured to generate the at least one marker and to display the at least one marker superimposed on the real-world view of the person during a first visit;
the system is configured to automatically display the at least one marker superimposed on another real-world view of the person during a second visit after the first visit; and
during the second visit, the at least one marker is displayed at a same location on the person's face as it was during the first visit to facilitate providing an injection at the same location on the person's face during both the first visit and the second visit.

23. A augmented reality (AR) system for administering injections, comprising:
an AR headset comprising a display that is configured to display at least one marker superimposed on a real-world view of a subject, the at least one marker being displayed at a user-defined location on the subject,
wherein the AR headset comprises a face mapping system, and
the location of the at least one marker on the subject is defined relative to a facial map of the subject generated by the face mapping system.

24. A method of using augmented reality (AR) for administering injections to a person, comprising:
receiving user input defining at least one marker at a location on the person;
displaying, by a display of an AR headset, the at least one marker superimposed on a real-world view of the person, the at least one marker being displayed at the user-defined location on the person, and the at least one marker defining a location of an injection into the person.

25. The method of claim 24, further comprising continuously displaying the at least one marker at the location on the person as the real-world view of the subject changes.

* * * * *